(12) United States Patent
Craig

(10) Patent No.: US 7,086,862 B2
(45) Date of Patent: Aug. 8, 2006

(54) TOOTH BLEACHING PROCESS

(75) Inventor: Lisa Craig, Los Angeles, CA (US)

(73) Assignee: Discus Dental, Inc., Culver City, CA (US)

( * ) Notice: Subject to any disclaimer, the term of this patent is extended or adjusted under 35 U.S.C. 154(b) by 316 days.

(21) Appl. No.: 10/715,681

(22) Filed: Nov. 17, 2003

(65) Prior Publication Data

US 2004/0152051 A1   Aug. 5, 2004

Related U.S. Application Data

(60) Provisional application No. 60/426,617, filed on Nov. 15, 2002.

(51) Int. Cl.
*A61C 5/00* (2006.01)

(52) U.S. Cl. .................. 433/215; 433/29; 433/140; 433/137; 600/242

(58) Field of Classification Search ............... 433/137, 433/215; 600/242; 378/168, 170, 191, 205
See application file for complete search history.

(56) References Cited

U.S. PATENT DOCUMENTS

| | | | | |
|---|---|---|---|---|
| 3,916,880 | A * | 11/1975 | Schroer | ............... 600/205 |
| 4,528,180 | A | 7/1985 | Schaeffer | |
| 4,687,663 | A | 8/1987 | Schaeffer | |
| 4,840,174 | A * | 6/1989 | Gluckman | ............... 606/15 |
| 4,849,213 | A | 7/1989 | Schaeffer | |
| 4,952,143 | A * | 8/1990 | Becker et al. | ............... 433/32 |
| 4,990,089 | A | 2/1991 | Munro | |
| 5,032,178 | A | 7/1991 | Cornell | |
| 5,713,738 | A | 2/1998 | Yarborough | |
| 5,718,886 | A | 2/1998 | Pellico | |
| 5,785,527 | A | 7/1998 | Jensen et al. | |
| 5,855,870 | A | 1/1999 | Fischer | |
| 5,858,332 | A | 1/1999 | Jensen et al. | |
| 5,902,568 | A | 5/1999 | Ryles et al. | |
| 5,922,307 | A | 7/1999 | Montgomery | |
| 5,928,628 | A | 7/1999 | Pellico | |
| 6,036,493 | A | 3/2000 | Sharma | |
| 6,036,943 | A | 3/2000 | Fischer | |
| 6,106,812 | A | 8/2000 | Prencipe et al. | |
| 6,110,446 | A | 8/2000 | Prencipe et al. | |
| 6,116,900 | A * | 9/2000 | Ostler | ............... 433/89 |
| 6,162,055 | A | 12/2000 | Montgomery et al. | |
| 6,322,773 | B1 | 11/2001 | Montgomery | |
| 6,332,776 | B1 * | 12/2001 | Martin et al. | ............... 433/140 |
| 6,343,933 | B1 | 2/2002 | Montgomery et al. | |
| 6,391,283 | B1 * | 5/2002 | Jensen et al. | ............... 424/49 |
| 6,416,319 | B1 | 7/2002 | Cipolla | |
| 6,448,914 | B1 | 9/2002 | Younis et al. | |

(Continued)

FOREIGN PATENT DOCUMENTS

WO    WO 98/10737    3/1998

(Continued)

*Primary Examiner*—Ralph A. Lewis
*Assistant Examiner*—Casey Donahoe
(74) *Attorney, Agent, or Firm*—Christie, Parker & Hale, LLP

(57) ABSTRACT

A system and method for tooth bleaching are disclosed wherein a patient's mouth is prepped for tooth bleaching treatment, a light activated tooth bleaching composition is applied on a tooth surface to be bleached, a lamp assembly is placed in position to activate the oxidizing compound in the bleaching composition, and one or more spacer is coupled to the patient and to the lamp assembly to set a distance between the two.

34 Claims, 10 Drawing Sheets

U.S. PATENT DOCUMENTS

| | | | |
|---|---|---|---|
| 6,485,301 B1 * | 11/2002 | Gemunder et al. | 433/29 |
| 6,503,485 B1 | 1/2003 | Allred | |
| 6,514,075 B1 * | 2/2003 | Jacob | 433/29 |
| 6,514,543 B1 | 2/2003 | Montgomery | |
| 6,536,628 B1 | 3/2003 | Montgomery | |
| 6,702,576 B1 | 3/2004 | Fischer et al. | |
| 6,733,290 B1 * | 5/2004 | West et al. | 433/29 |
| 6,880,954 B1 * | 4/2005 | Ollett et al. | 362/245 |
| 2003/0198605 A1 | 10/2003 | Montgomery | |
| 2004/0076926 A1 * | 4/2004 | Baughman | 433/215 |
| 2004/0152051 A1 | 8/2004 | Craig | |
| 2005/0048434 A1 | 3/2005 | Cipolla et al. | |
| 2005/0084826 A1 * | 4/2005 | Pilaro et al. | 433/215 |
| 2005/0265933 A1 | 12/2005 | Montgomery et al. | |

FOREIGN PATENT DOCUMENTS

| | | |
|---|---|---|
| WO | WO 98/30494 | 7/1998 |
| WO | WO 99/62472 | 12/1999 |
| WO | WO 00/16737 | 3/2000 |
| WO | WO 00/28953 | 5/2000 |
| WO | WO 01/17481 | 3/2001 |

* cited by examiner

TOOTH BLEACHING PROCESS

CROSS-REFERENCE TO RELATED APPLICATION

This is an ordinary application of provisional application Ser. No. 60/426,617, filed Nov. 15, 2002, entitled "TOOTH BLEACHING PROCESS", its contents are expressly incorporated herein by reference.

The present invention pertains generally to methods for whitening teeth, particularly those involving application of a whitening composition to a patient's teeth, followed by exposure of the teeth and composition to light from a lamp. The method described herein is generally intended to be performed under controlled conditions in a dental office.

BACKGROUND

Tooth bleaching is well known in the art. Generally speaking, a typical tooth bleaching process involves preparing a patient's teeth for application of a light activated tooth bleaching composition. A light, of certain light spectrum range, is then radiated on the composition to activate the oxidizing agents to thereby bleach the teeth.

While there are variations in the bleaching compositions and the types of light used to activate the compositions in the prior art, the process of applying a light source on a patient to activate the bleaching composition is arguably uniform. Typically, a patient will be requested to remain still in a reclined position while a light source is shined in the mouth area to activate the bleaching composition for the one or more light activation treatment periods. Ideally, during these treatment periods, light radiation is focused on a target area for the duration of the treatment period. The target area usually consists of the prepped area of the teeth to be bleached. However, uncontrollable movements and intentional movements by the patient will often occur during these treatment periods to cause the light to deviate from the target area. When this occurs, inadequate bleaching and, in some cases, injuries can occur to the facial and unprotected gum area of the mouth.

Accordingly, there is a need for an apparatus and a method for regulating or controlling the movement of the patient relative to a light source during a tooth bleaching procedure using a light activated composition and a light assembly.

SUMMARY OF THE PREFERRED EMBODIMENTS

According to the present invention, there is provided a method for whitening a patient's teeth comprising the steps: (a) applying a dental whitening composition to the teeth; (b) illuminating the teeth with light from a lamp assembly; and (c) wherein the lamp assembly is maintained in a constant position relative to the teeth by a lamp guide comprising a first end and a second end, wherein the first end of the lamp guide is coupled, either directly or indirectly, to the patient, and the second end of the lamp guide is coupled to the lamp assembly.

In another aspect of the present invention, there is provided a system for tooth bleaching comprising: (a) a bleaching composition comprising an oxidizing agent; (b) a lamp assembly comprising a light source, a light output aperture and an engagement surface; (c) a gap regulating device; and (d) wherein the bleaching composition is configured to be applied on a tooth surface of a patient and the gap regulating device is configured to couple to the patient and to the engagement surface of the lamp assembly to set a distance between the light output aperture and the tooth surface to be bleached.

In yet another aspect of the present invention, there is provided a system for tooth bleaching comprising: (a) a tooth bleaching composition comprising an oxidizing agent; (b) a lamp assembly comprising a lamp head and a power supply box mounted on a lamp post comprising an adjustable hinge; (c) a spacer for setting a space between the lamp head and a patient's teeth; and (d) wherein the tooth bleaching composition is configured to be applied to a tooth surface to be bleached, the lamp assembly is configured to activate the oxidizing agent from the tooth bleaching composition; and the spacer is configured to set a gap between the lamp head and the patient's teeth by coupling to both the patient and the lamp head.

BRIEF DESCRIPTION OF THE DRAWINGS

These and other features, aspects and advantages of the present invention will be more fully understood when considered with respect to the following detailed description, appended claims and accompanying drawings, wherein:

DETAILED DESCRIPTION OF THE PREFERRED EMBODIMENTS

The detailed description set forth below in connection with the appended drawings is intended as a description of the presently preferred tooth bleaching process provided in accordance with aspects of the present invention and is not intended to represent the only forms in which the present invention may be constructed or utilized. The description sets forth the features and the steps for performing the tooth bleaching process of the present invention in connection with the illustrated embodiments. It is to be understood, however, that the same or equivalent functions and structures incorporated in the tooth bleaching process may be accomplished by different embodiments that are also intended to be encompassed within the spirit and scope of the invention.

As denoted elsewhere herein, like element numbers are intended to indicate like or similar elements or features.

The first stage of the method in accordance with aspects of the present invention preferably involves isolation of the teeth and protection of the non-tooth surfaces that might otherwise be exposed to the bleaching composition in the absence of protection.

In one embodiment, a commercially available protective lip cream is applied to the lips to protect the lips. A cotton swab may be used to coat the lips with the cream. The cream is configured to keep the lips moist during the procedure and provide added protection from light exposure. Exemplary protective lip creams include paba free creams with high SPF rating, of about 30 or higher SPF.

Figure 1:
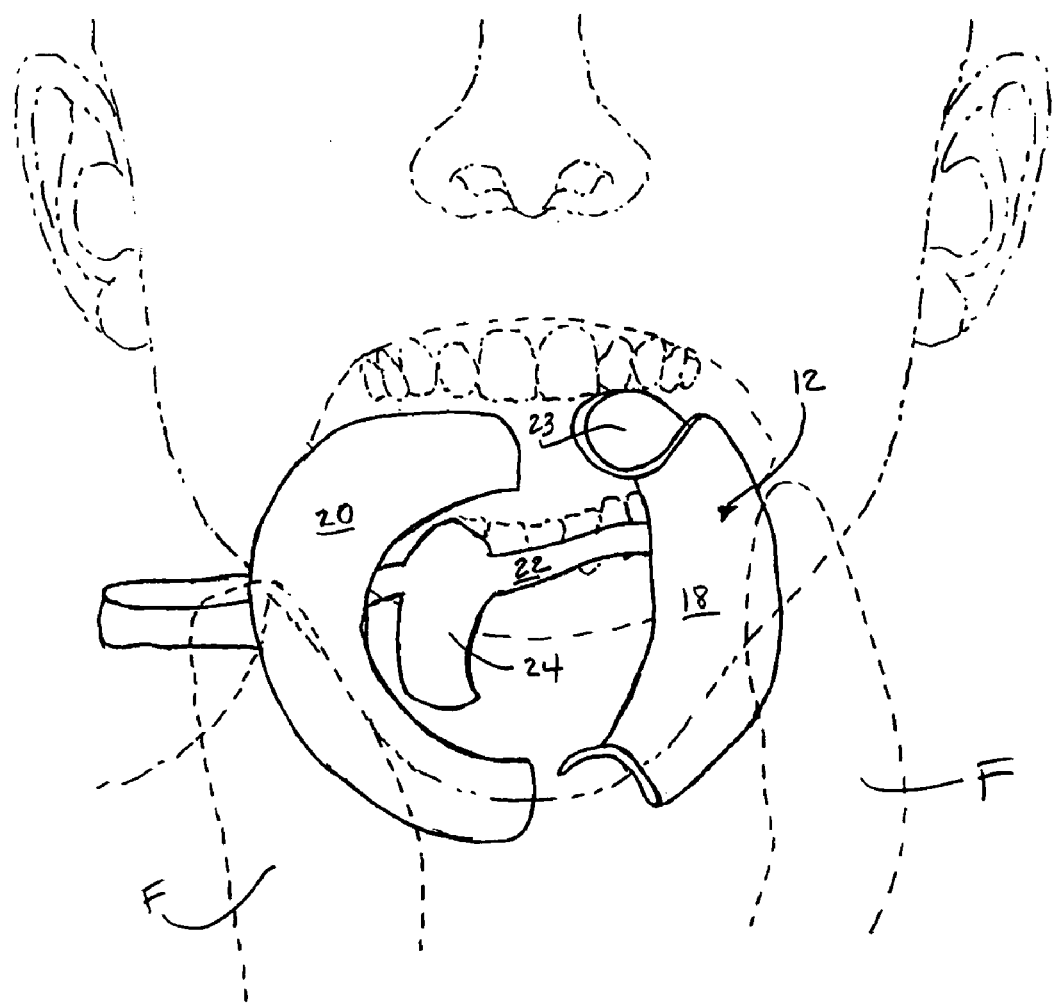
FIG. 1 is a semi-schematic front view of a lip retractor provided in accordance with aspects of the present invention in a compressed configuration just before insertion into the mouth of a patient to retract the patient's lips.
Figure 2:
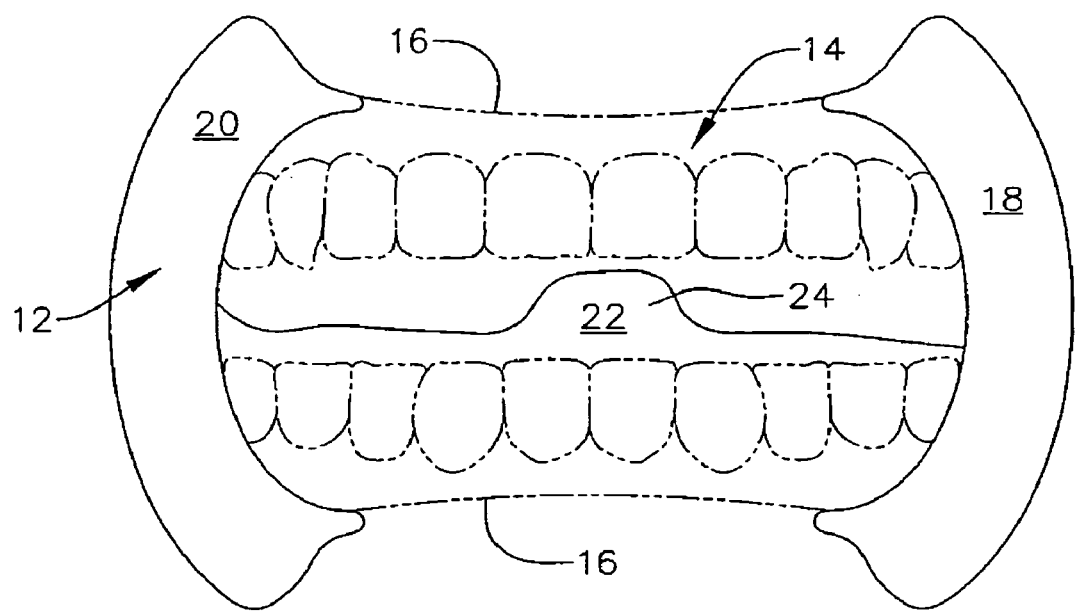
FIG. 2 is a semi-schematic view of the lip retractor in a retracted position inside a patient's mouth.

Next, a lip retractor 12, such as the ZOOM!™ Retractor from Discus Dental, Inc., of Culver City, Calif., is installed to pull the lips away from the teeth, as shown in FIGS. 1 and 2. In particular, FIG. 1 shows the lip retractor 12 squeezed together by a user's fingers F prior to inserting the same into a patient's mouth and FIG. 2 shows the lip retractor 12 in the retracted position inside the patient's mouth 14 retracting the lips 16.

Referring again to FIGS. 1 and 2, the lip retractor 12 (available from Glenroe of Brandenton, Fla.) provided in accordance with aspects of the present invention generally comprises a pair of cheek plates 18, 20 connected to one another by a flexible cross-bar 22. The cross-bar 22 includes a tongue guard 24 for occluding the tongue from interfering with the bleaching process. The retractor 12 may be made by injection molding a thermoplastic material such as polypropylene, polyethylene, polystyrene, or the like. Each cheek plate is adapted to surround or cup around one side of the mouth so that together the cheek plates 18, 20 retract the two sides of the mouth away from the teeth due to the biasing action of the resilient cross-bar 22. In one exemplary embodiment, the cheek plates 18, 20 each comprises an arcuate race 23 configured to cup the sides of the lips, where the upper and lower lips come together. The arcuate race is bounded by an interior side wall and an exterior side wall. The resilient cross-bar 22 is attached to the interior side walls of both cheek plates 18, 20.

Figure 5:
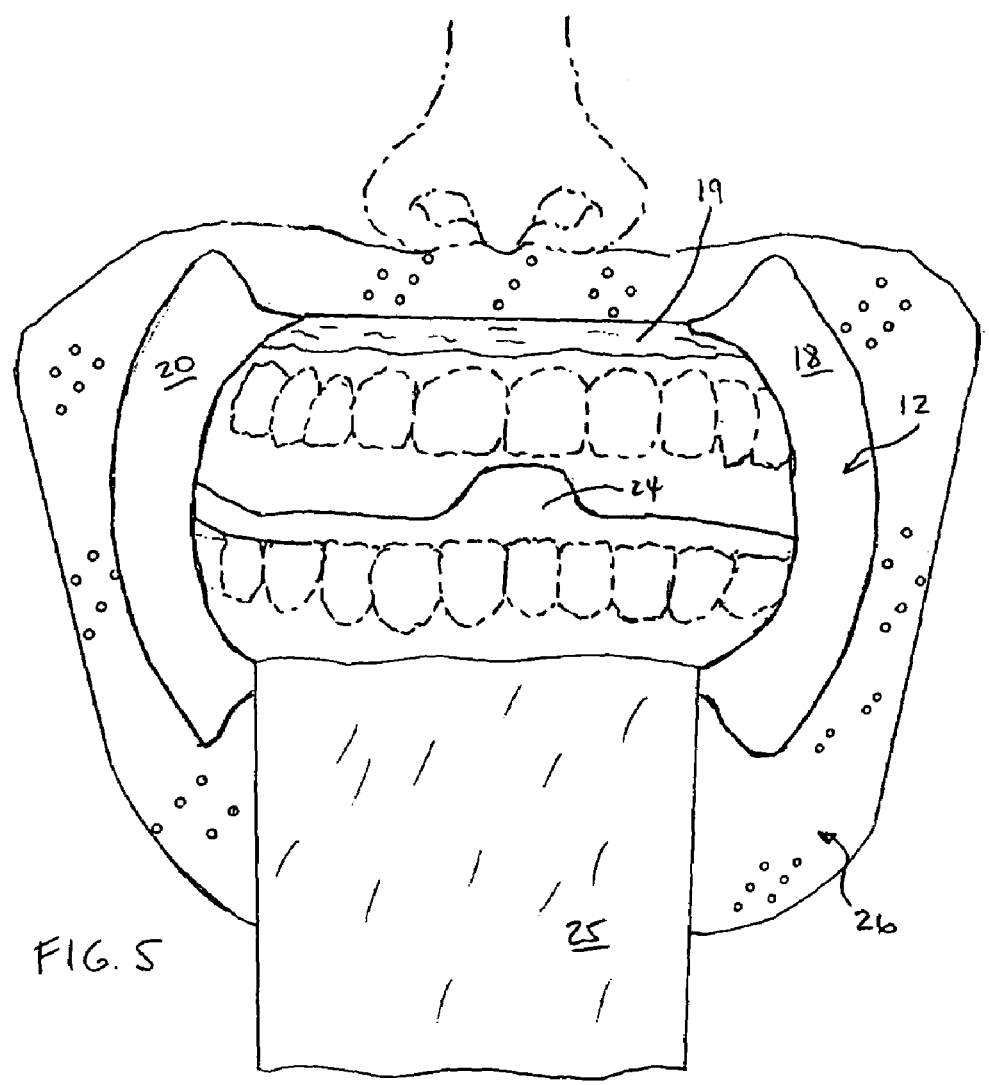
FIG. 5 is the semi-schematic view of FIG. 4 with a protective gauze.

The arc dimension of each arcuate race should be sufficient to retract portions of the upper and lower lips outwardly apart. Once the retractor 12 is in place, the patient should be asked to bite down on the cross-bar 22 and to rest his or her tongue against the tongue guard 24. The cross-bar 22 should extend sufficiently deep into the back of the mouth area to restrict movement of the tongue and provide access to the desired molars otherwise blocked by the tongue. In one exemplary embodiment, the cross-bar 22 should rest on the second molar. Cotton rolls 19 may be used to further retract the upper or lower lips if needed (FIG. 5). However, four-ply or other dense gauze is more preferred.

In an alternative embodiment, a retractor comprising four cheek plates and an optional tongue guard as described in application Ser. No. 10/371,665, filed Feb. 21, 2003, entitled RETRACTORS, may be used with the tooth bleaching process described herein. The contents of the '665 application are expressly incorporated herein by reference. In one exemplary embodiment, the lip retractor 12 and the alternative lip retractor are preferably opaque to protect the gum and lips from light radiation.

Figure 3:
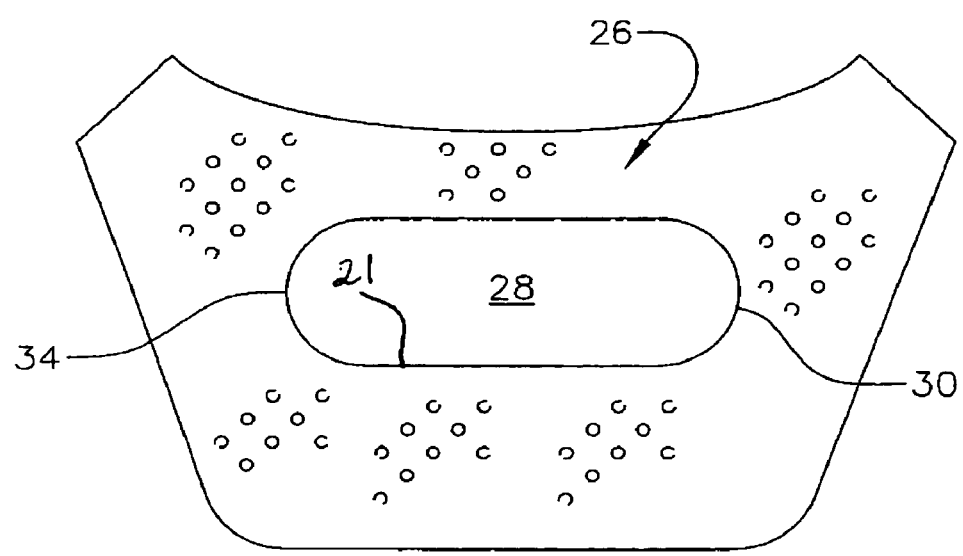
FIG. 3 is a semi-schematic view of a retractor cover for covering portions of a patient's face adjacent the lip retractor.
Figure 4:
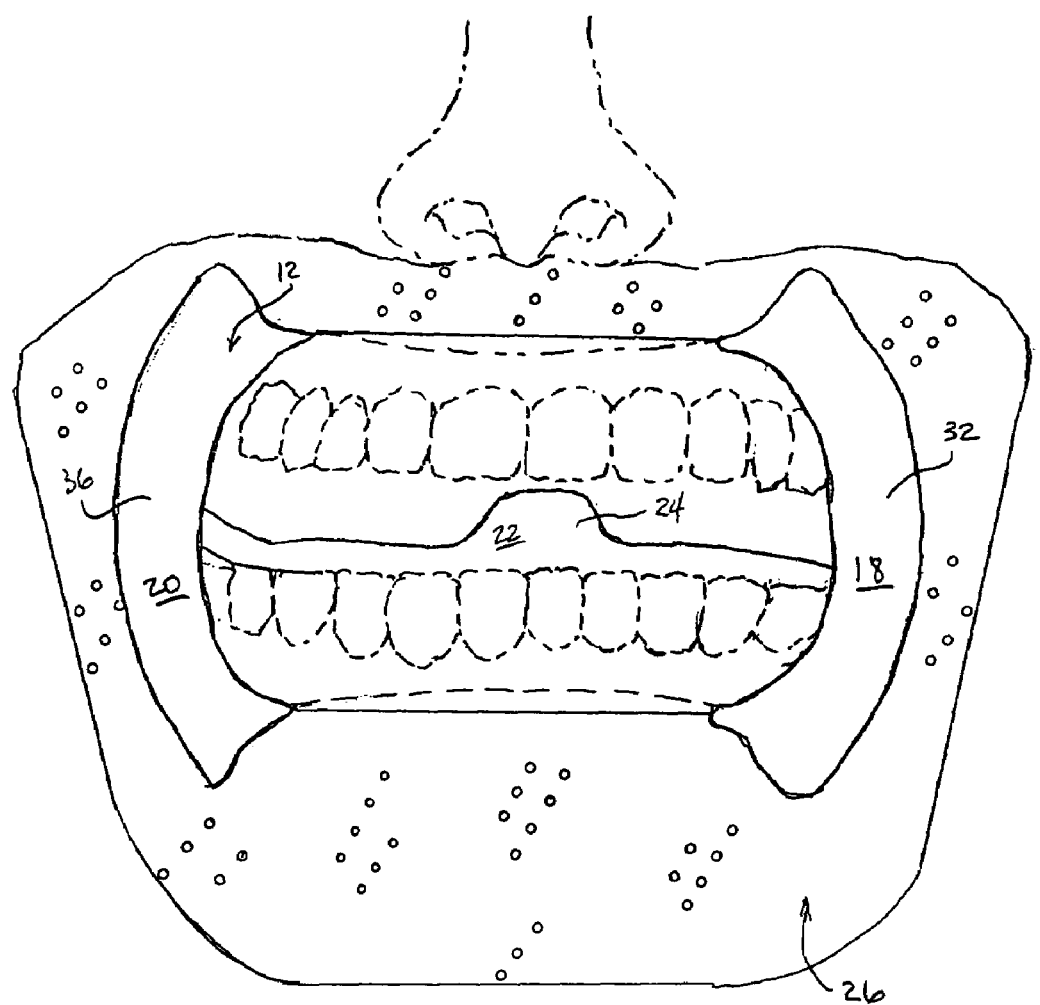
FIG. 4 is a semi-schematic view of the retractor cover in position on a patient's face.
Figure 6:
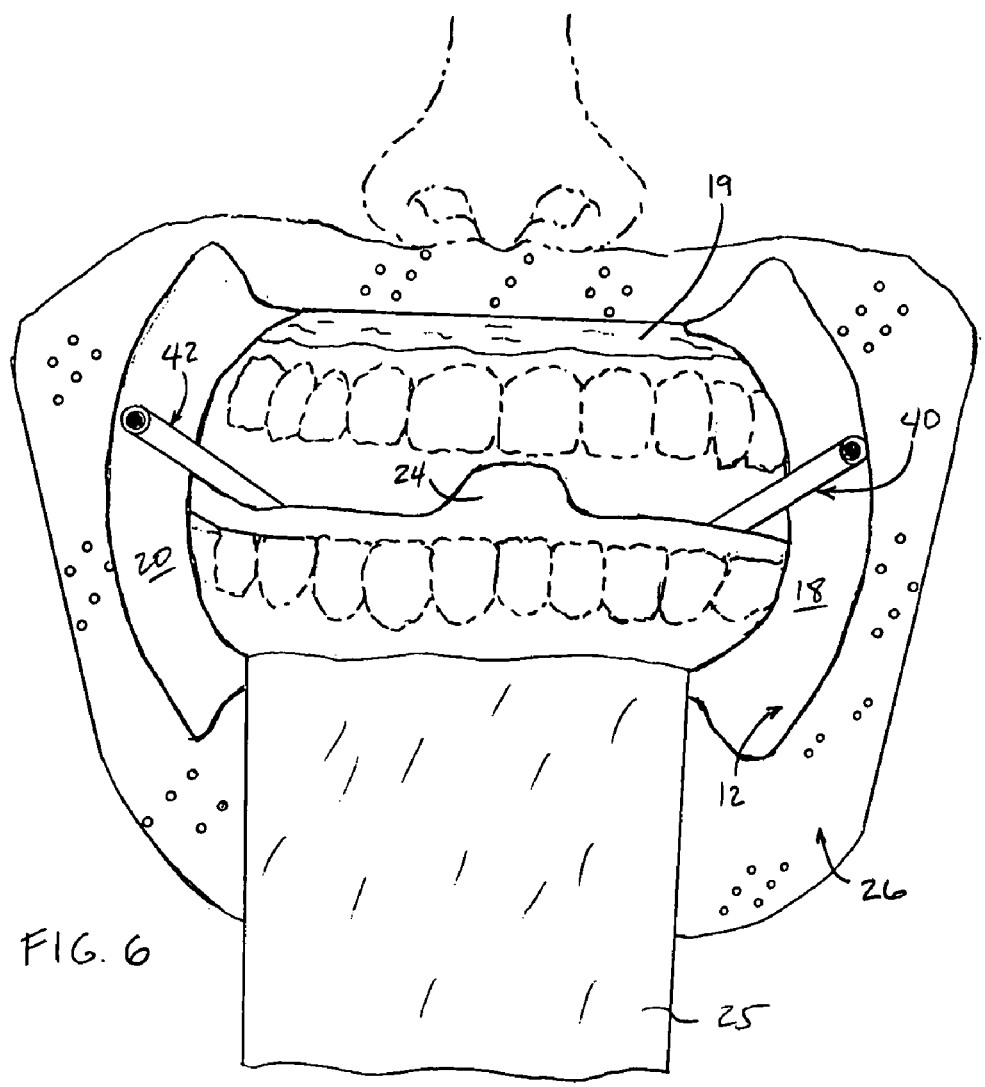
FIG. 6 is the semi-schematic view of FIG. 5 with a pair of light guides.

A retractor cover 26 (available from Coltene Whaledent of Cuyahoga Falls, Ohio) is preferably used to cover the patient's face beyond the perimeter of the retractor 12, as shown in FIGS. 3–6. As shown in FIG. 3, the retractor cover 26 may be a generally flat piece of dense four-ply gauze or other flexible fabric or material capable of protecting the face. An opening 28 is incorporated to fit around the cheek plates 18, 20 of the retractor 12, as shown in FIGS. 4–6. The retractor cover 26 is mounted over the lip retractor 12 by wedging a first opening end 30 under a side wall 32 of the cheek plate 18 and then a second opening end 34 under a side wall 36 of the other cheek plate 20. The installation may also be performed starting from the second opening end 34 of the opening 28. Preferably, the lower ledge 21 of the opening 28 is tucked inside the arcuate races of the two cheek plates 18, 20 so that the portion of the retractor cover adjacent the lower ledge 21 covers and protect the lower lip. Once in position (FIG. 4), the retractor cover 26 acts as a bib to protect the patient against splatter, light exposure, and irritation by the whitening gel.

For additional isolation, the dentist can use 2"×2" four-ply gauze squares, cotton rolls, or other suitable materials having suitable size to cover any remaining exposed tissues within the oral cavity. For example, in certain situations, the lip retractor 12 may cause the lower and/or upper lip to extend into the light target area by pushing the lower and/or upper lip outwardly. In these situations, a 2"×2" or other suitably sized gauze 25 may be placed over the lower lip for added protection, as shown in FIG. 5. The gauze may be adjusted by opening the ply into a 2"×4" or 4"×4" gauze and applied over the soft tissue area to isolate the same from the light.

A protective material is preferably applied to the gingiva to further protect the gums from exposure to the bleaching composition and the light radiation to be applied thereon. Preferably, a light-cured dental resin, such as Discus Dental's Liquidam™ Dental Dam, should be applied and cured as shown in FIG. 5. The gingiva should be dried prior to application of the protective material. The protective materials, which is generally a light curable resin-based material, is preferably syringed directly onto the gingiva with sufficient amount for full gingival protection. The application should extend distal at least one tooth beyond the area to receive the bleaching application. The application should also extend up or down to meet the gauze or retractor cover to protect the margins.

Figure 8:
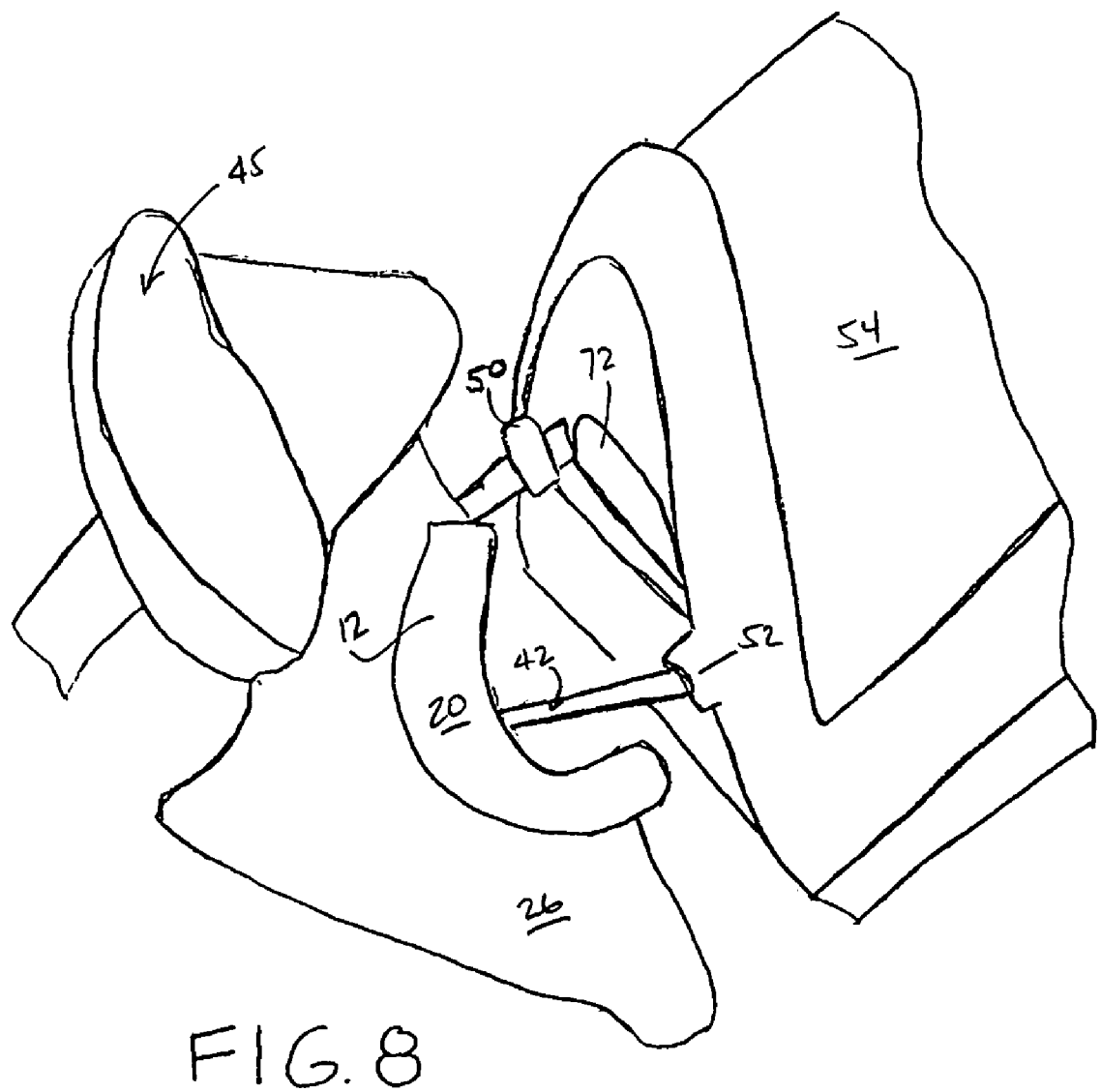
FIG. 8 is a partial semi-schematic perspective view of the light guides of FIG. 7 inside a patient's mouth setting a gap between the patient and the light head assembly.

As previously set forth, exposed dentin should be covered by the Liquidam™ isolation material, or other similar light-cured dental resin, to help prevent irritation caused by the tooth whitening gel. Liquidam™ is a viscous liquid that can be applied to no less than about one quadrant at a time. Any number of commercially available curing lights may be used to cure the material. Ten seconds is typically needed to cure an entire arch, which can vary in time depending on the particular product used and the particular lamp applied to the isolated material. The dentist should cure the protective material for approximately 1 second above each tooth or alternatively use a sweeping motion across the arch of the row of teeth for the 10 second cycle. Once polymerized, the cured material will still appear wet as a thin layer of oxygen inhibited resin formed on the surface has a shinny reflective layer. The dentist can tap or touch the cured protective material to ensure it has completely polymerized into a solid form. If necessary, the dentist can cure the application again for an additional few seconds, but taking care not to over cure the resin material as it may retain heat and may cause discomfort to the patient. For additional information, instructions that come with the protective material should be followed. For safety, an eye protective gear 45 (FIG. 8)

should be worn on the patient before applying the bleaching composition and before curing the protective material with a light source. Preferably, the Dentist and his/her assistants should also wear protective gear. The protective gear should be commensurate with the light source used, which can vary from an argon laser to a charged gas lamp.

Once the application of the dental dam is complete, the margins should be rechecked to ensure that the dam is sealed against the enamel to prevent leakage and oxidation of tissue during the whitening procedure.

Figure 7:
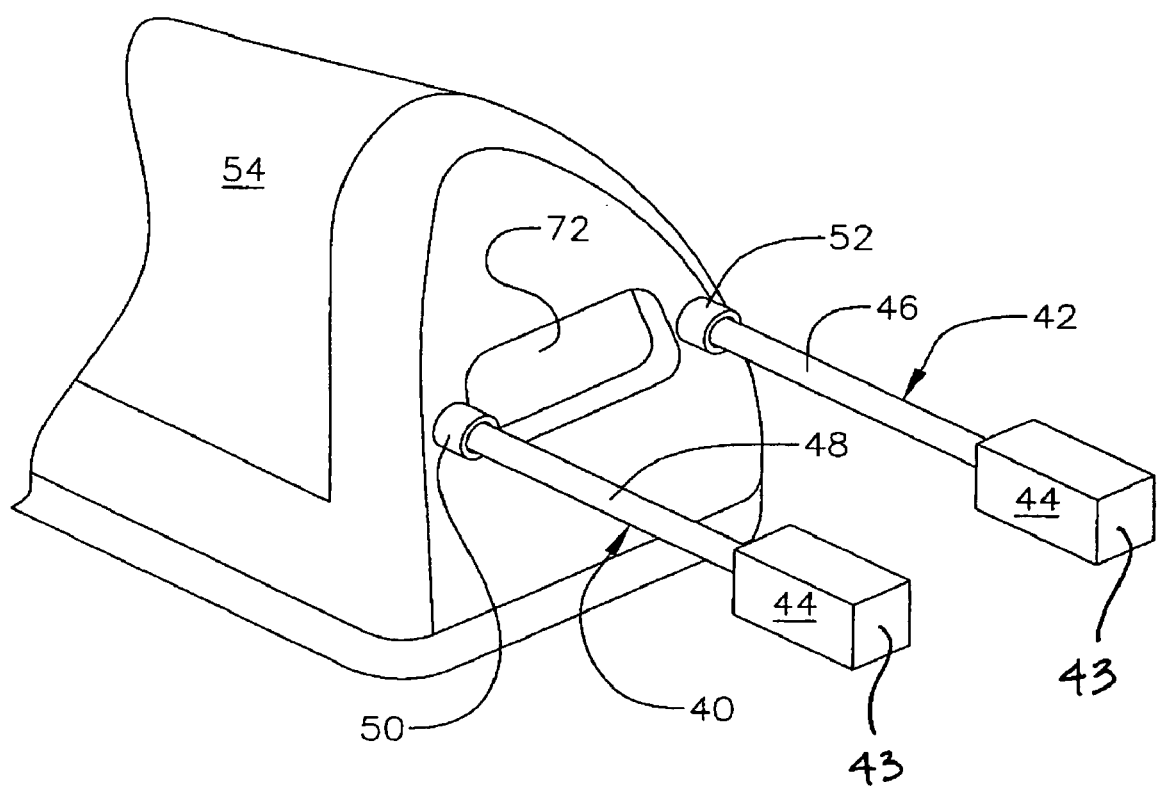
FIG. 7 is a partial semi-schematic perspective view of the light guides of FIG. 6 attached to a light assembly.

Next, a pair of light guides or spacers 40, 42 is coupled to the patient by, for example, inserting their respective ends into the patient's mouth (FIG. 6). Each light guide includes a foam bite pad 44 at one end of an extended post 46, 48 (FIG. 7). Each bite pad 44 is configured to be positioned between the patient's molars on each side of the mouth so that the rectangular areas of the pads lay between each set of molars. In one exemplary embodiment, the light guides 40, 42, including the bite pads, are each about 2.5 inches in length from end to end. To control or regulate the length of the light guides 40, 42 that extend from the inside of the mouth to the outside of the mouth, the ends 43 (FIG. 7) of the bite pads 44 should be placed flushed against the cross-bar 22. Furthermore, the two posts 46, 48 should extend out of the mouth along the corresponding edge of the cheek retractor 12, (FIG. 6).

The ends of the light guides 40, 42 that extend out of the mouth are eventually inserted into corresponding bores or bosses 50, 52 on the front of the lamp head 54 (FIG. 7) during the bleaching process. In one exemplary embodiment, the light guides extend about 1.5 inches out of the patient's mouth. However, the length of the light guides and the length that extends outside of the mouth can vary depending on the dentist, the bleaching composition and the light assembly used.

Positioning the lamp head 54 to the patient via the light guides 40, 42 will enable the position of the lamp to be fixed relative to the patient's teeth, as further discussed below. In an alternative embodiment, the retractor 12 can have bosses molded adjacent the cheek plates 18, 20 and the light guides, without the foam bite pads 44, engage the bosses.

Before the lamp is positioned relative to the patient's teeth, the bleaching composition is first applied onto the tooth surfaces for which whitening is desired. A variety of different bleaching compositions have been developed in the prior art for use in conjunction with light assemblies. An exemplary composition is that sold by Discus Dental of Culver City, Calif., under the Zoom! trademark, which includes two components provided in separate chambers of a dual barrel syringe. The first component is a "bleaching" gel that comprises the following (on an approximate weight % basis):

| | |
|---|---|
| i. glycerin | 2% |
| ii. water | 2.65% |
| iii. hydrogen peroxide (50% CG) | 64% |
| iv. Pluronic 127 | 28% |
| v. eugenol | .75% |
| vi. natural peppermint oil | 1.1% |
| vii. potassium nitrate | 1.5% |

The second component is an "activator gel" that comprises the following (on an approximate weight % basis):

| | |
|---|---|
| i. deionized water | 38.7% |
| ii. Pluronic 127 | 21.5% |
| iii. polydimethylsiloxane | QS |
| iv. glycerin | 9.6% |
| v. deionized water | 14.2% |
| vi. potassium hydroxide | 4.9% |

Immediately before use, the two components are mixed together in a 4:1 ratio (bleaching gel to activator gel) by actuating the syringe. The whitening gel is applied to the surface of the teeth directly from the syringe, approximately 1–2 mm thick. A brush may be used to ensure proper placement of the gel. Alternatively, the bleaching composition may be dispensed into a dappen dish or into a mixing pad for placement onto the tooth surface with a brush. If contact occurs between the whitening gel and tissue during application of the bleaching composition, Vitamin E Oil can be applied to the oxidized tissue. The oil material will help sooth the tissue and create a barrier so that the whitening procedure can continue. As readily apparent, although the Zoom! Product is discussed above with particularity, any light activated bleaching composition may be practiced using the disclosed bleaching process provided in accordance with aspects of the present invention. In addition, while a two-part bleaching composition stored inside a dual barrel syringe is disclosed, a pre-mixed one part light activated bleaching composition may also be used with the present system.

Once the whitening gel application is applied, the light assembly 53 can be moved into position to activate the gel. If the light assembly 53 has been used on other patients, the timer can be turned on and activated immediately. If the light assembly has not been in operation, a warm up cycle may be required. With reference to FIG. 8, the back of the chair that the patient sits on should be raised so that the patient is in a slightly reclined position and able to comfortably swallow. The light head 54 should be positioned so that the entire smile zone may be completely exposed to the light radiation emitted from the housing aperture 72 (FIGS. 7 and 8). The light incident on the patient should be focused on the teeth and should not extend above the margin to the dam application. The exposed tips of the guide posts 40, 42 should then be attached to the bosses 50, 52 or other suitable engaging means on the front of the light head 54. The guide posts 40, 42 should be lightly pushed into the bosses 50, 52 (FIG. 8) until the fit is secured, as shown in FIGS. 7 and 8. As readily apparent, any of a variety of structures or linkages can be used to engage the guide posts to the lamp, so long as the position of the lamp relative to the patient's teeth is constant. When assembled properly, the light should rest about 1.5 inches (3.3 cm) from the buccal surface of the maxillary central incisors. However, for a particular light assembly, the distance can vary due to the output power, the light or lamp used, and the angle of incident of the light rays.

Once the light head is secured in place and the smile zone illuminated, the whitening cycle can begin by activating the light. For the composition described above, this will involve an approximately 20-minute cycle. If the light assembly has not been used, a warm up cycle of a few minutes may first be required. At the end of the cycle, the light guides should be detached from the light head and then subsequently the light head can be swung away from the patient to provide comfortable access. The gel should be suctioned from the patient's teeth and any remaining gel removed with a dampened gauze.

For the bleaching composition and light assembly described, a second and a third application of the whitening gel and light curing cycle are preferred. However, for other bleaching composition and light source, the number of applications can vary.

After the final cycle has been completed, the light guides are detached from the light head and the light is removed from the patient. The remaining whitening gel is suctioned and wiped from the teeth. The isolation materials (gauze, cotton rolls, gingival protection) are then removed and, with the retractor in place, the oral cavity is thoroughly rinsed and suctioned. Dental floss can be used to remove any dental resin material that remains interproximally.

With the retractor still in place, various post-treatment procedures can be carried out. For example, the facial area of the teeth can be dried and a fluoride solution (such as 1.1% Neutral Sodium Fluoride) can be applied, preferably by syringing it directly onto the teeth, approximately 2–3 mm thick, and allowing it to remain on the teeth for about 5 minutes before suctioning and rinsing.

Light Assembly

Figure 10:
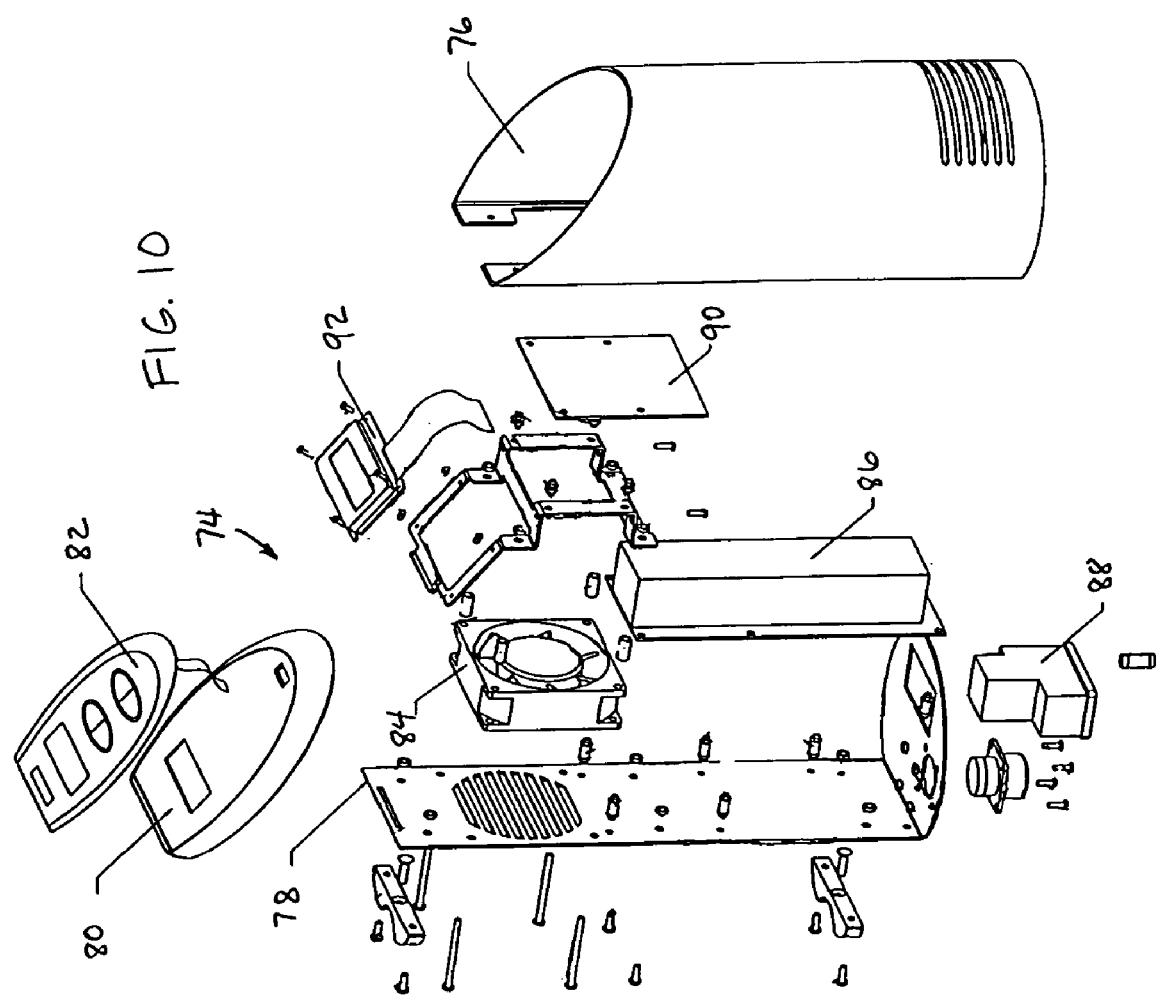
FIG. 10 is a semi-schematic exploded view of a power supply assembly for powering the light head assembly of FIG. 9.
Figure 11:
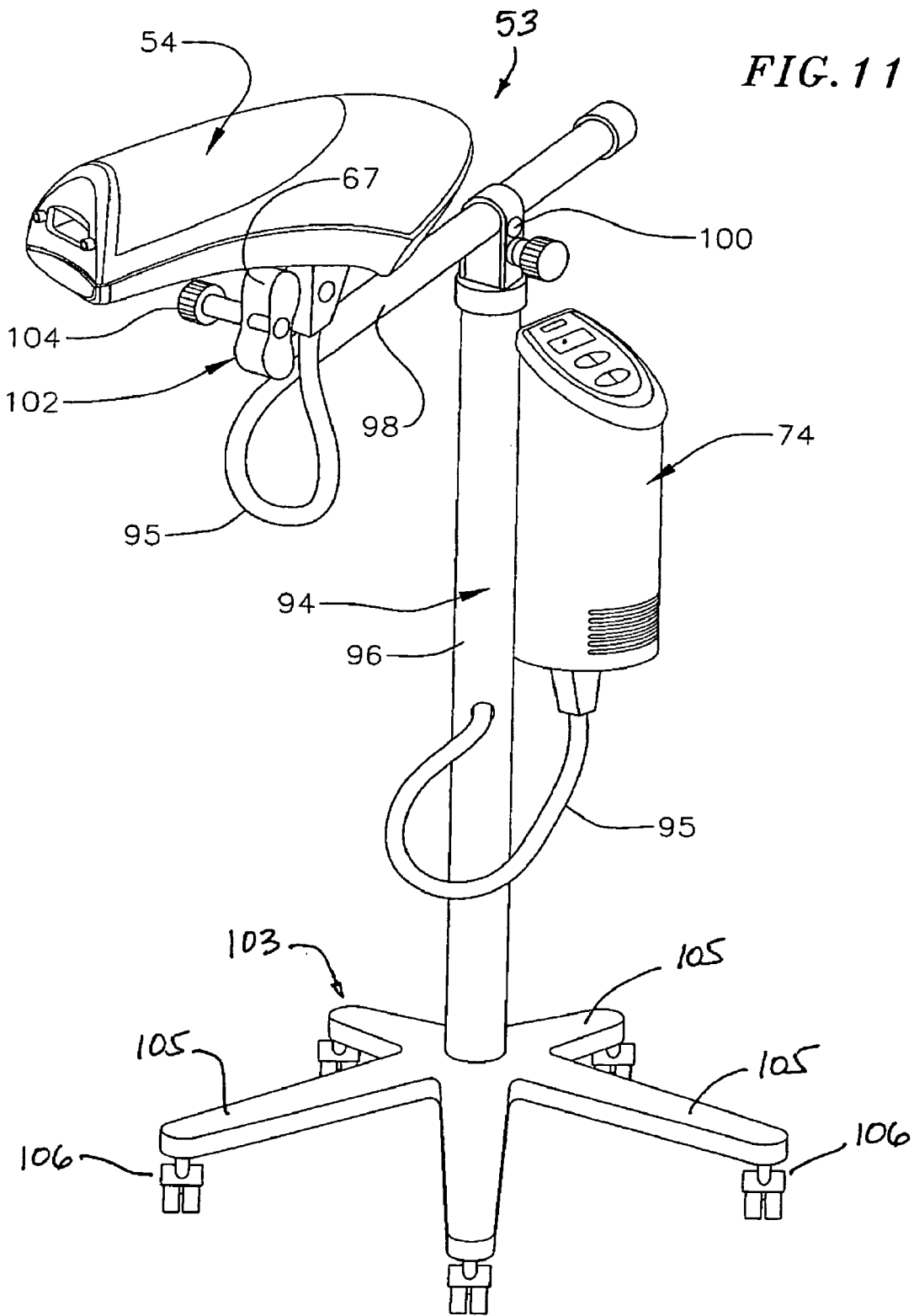
FIG. 11 is a semi-schematic perspective view of the light head assembly of FIG. 9 and power supply assembly of FIG. 10 mounted on a light stand.

Three schematic diagrams of the light assembly 53 are attached, one directed to the light head assembly 54 (FIG. 9), one to the power supply assembly 74 (FIG. 10), and one to the mounting of the light head assembly 54 and the power supply assembly onto a light stand (FIG. 11). Although the light assembly 53 is disclosed herein below with particularity, other curing lamps having suitable light properties may be used with the tooth bleaching process provided in accordance with aspects of the present invention.

Figure 9:
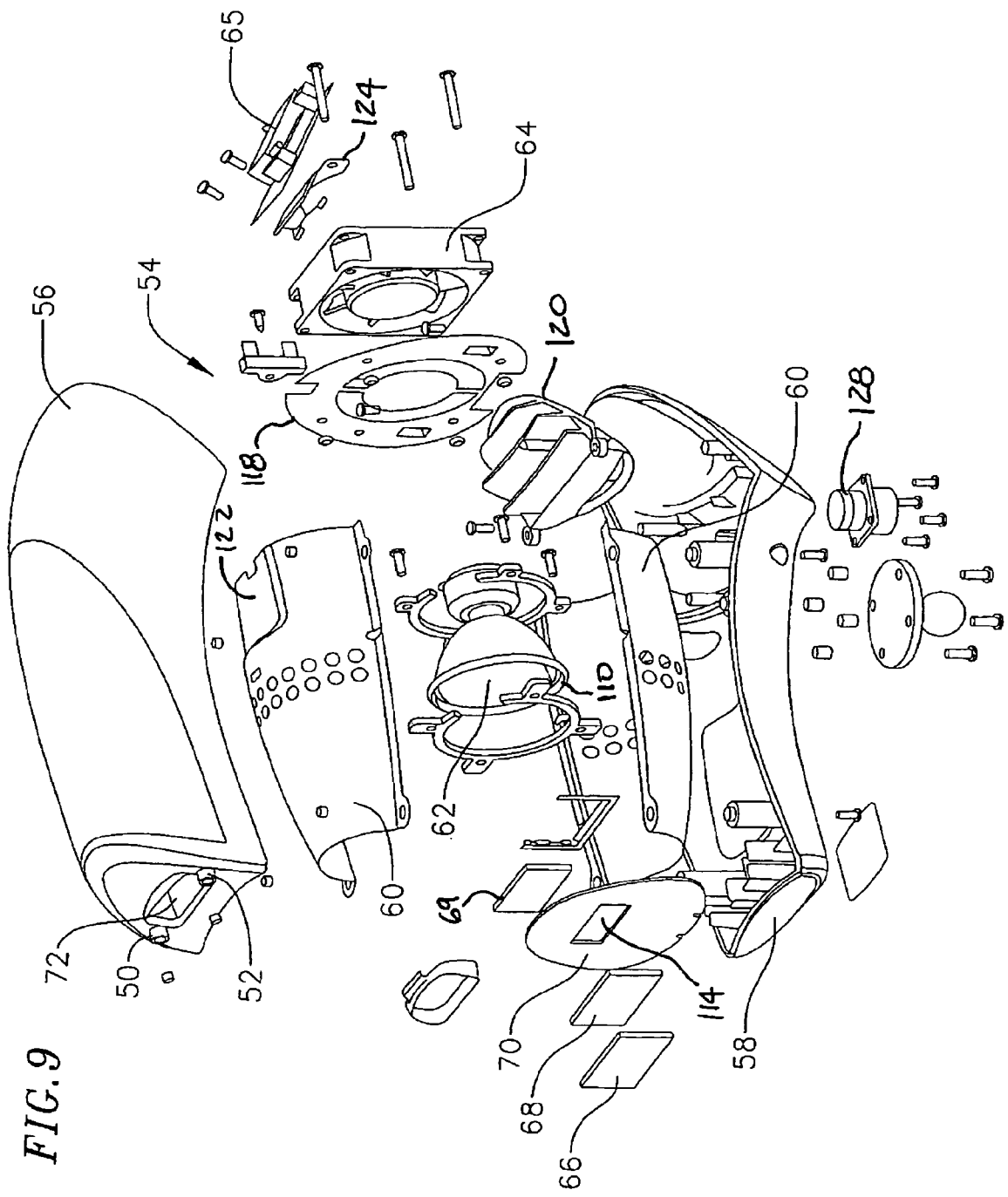
FIG. 9 is a semi-schematic exploded view of the light head assembly of FIG. 8.

Referring specifically to FIG. 9, the light head assembly 54 has a top housing cover 56 and a bottom housing cover 58, which together define a housing. The housing may be made from a hard plastic material, such as ABS, polycarbonate, polyethylene, CPVC, or other suitable plastics. The upper and lower housing covers 56, 58 are molded with ridges, ribs, and other anchoring means for fastening and fixing various hardware components to the housing. The upper and lower housing covers 56, 58 are available from Peerless Injection Molding of Torrance, Calif.

Contained within the housing is a metal heat shield 60 configured retain various hardware components and to absorb heat emitted from the lamp 62. In one exemplary embodiment, the heat shield is made from a 1100-0 aluminum material or equivalents and coated with black textured powder to absorb heat. A plurality of heat exhaust openings 112 are provided in the heat shield 60 to prevent gas build up and to facilitate circulation. The metal heat shield is available from Specialized Welders of Torrance, Calif., part Nos. 03-1101 and 03-1019.

A lamp 62 and lamp support brackets are housed within the heat shield 60. The lamp 62 is a short arc metal halide lamp potted in a 3-inch diameter elliptical filter with a dichroic coating. An exemplary suitable lamp is the SMR-150UV1, Model No. 04-1001, from Ushio America, Inc., of Cypress, Calif.

Three filters are placed in front of the lamp; which includes the UV filter 66 (available from Optical Industrial of Houston, Tex., Part No. 03-1013), the IR filter 68 (available from Swift Glass of Elmira, N.Y., part No. 03-1017), and the diffuser filter 69 (available from Edmund Industrial Optics of Barrington, N.J., part No. 03-1020). The IR filter 68 is configured to filter all IR wavelengths to thereby reduce heat emitted to the patient. While the IR filter is configured to inhibit any output from the heat generating portion of the spectrum, due to radiation from the housing and possibly defects in the filter, some UV light may pass through the filter. In one exemplary embodiment, the IR filter is placed between the lamp and the UV filter to protect the UV filter from excess heat.

The UV filter 66 is configured to remove some, but not all, of the ultraviolet wavelengths. Preferably, UV wavelengths below about 345 nm are filtered by the UV filter 66 and only about 10–15% of wavelengths above about 400 nm are allowed to pass through the filter. The diffuser filter 69 is configured to diffuse the light rays and minimize the intensity of light irradiating onto the target area of the mouth. In one exemplary embodiment, the edge 110 of the lamp 62 is positioned about 118 mm from the diffuser filter.

With regard to the UV filter 66, the emitted radiation is filtered by a 3 mm thick KG-3 infrared filter plus a 3 mm Kopp-52 Ultraviolet (UVB/UVC) filter. The emitted radiation is projected through a housing aperture 72 having a dimension of about 0.75 by 2.15 inches, which is located at the end of the upper housing cover 56. The housing aperture limits the radiation pattern to the teeth by its physical opening to prevent unwanted irradiation to the other parts of the mouth.

The optical emission at a working distance of 1.5 inches has been measured. The following irradiances were measured:

UVC (250–290 nm) $1.96 \times 10^{-8}$ W/cm$^2$
UVB (290–320 nm) $1.01 \times 10^{-8}$ W/cm$^2$
UVA2 (320–340 nm) $7.64 \times 10^{-7}$ W/cm$^2$
UVA1 (340–400 nm) $4.41 \times 10^{-2}$ W/cm$^2$ A metal aperture 70 is placed between the diffuser filter 69 and the UV/IR filters 66, 68. The metal aperture 70 has an opening 114 of about 0.75 inch by 2.15 inch rectangular dimension. The metal aperture 70 further restricts diffused light rays passing through the diffuser filter 69 so that only rays projected through the opening 114 are permitted to pass through to the downstream filters. A diffuser bracket 116 comprising a channel may be used to hold the diffuser filter 69 within the heat shield 60.

Rearwardly of the lamp 62 are a fan bracket 118, a fan 64, and a light head screen bracket 120. An igniter PCB 65 (available from Hansmann Electronics GmbH Company KG of Barsinghausen, Germany, ZG5L P.C.B. Igniter, part No. 04-1002) is mounted to the rear seat 122 of the upper metal shield 60 and secured in place by an igniter bracket 124. A thermal fuse 126 (available from Hansmann Electronics GmbH Company KG, P.S.M ELDC2.3-I, part No. 04-1010) is incorporated to protect the light assembly from overheating. The thermal fuse 126 should be selected in accordance with general safety practice. In one exemplary embodiment, the thermal fuse is selected to power down or shut off the lamp when about 185 degrees F. is reached. Once the temperature falls below about 154 degrees F., the lamp may be restarted. In one exemplary embodiment, the power setting for the lamp may be set to operate at about 140 watts to 200 watts variable power input depending on the selected setting by the end user.

A pin connector 128, such as a 7-pin connector available from DSM&T of Fontana, Calif., part No. 04-1005, may be used for communicating the lamp head assembly 54 with the power supply assembly 74. A ball mounting plate 67 comprising a plastic ball may be used to mount the lamp head assembly 54 to the light stand 94 (FIG. 11) in a ball-and-socket type arrangement.

Power Supply Assembly

Turning to FIG. 10, the power assembly 74 includes an outer housing cover 76, a chassis 78, and a cap 80. A membrane keypad 82 available from Comstar Industries of Santa Ana, Calif., part No. 04-1008, is positioned on the cap 80 for user I/O operation. Within the housing 76, there is a fan 84, a power supply module 86 (available from Hansmann Electronics GmbH Company KG of Germany, part No. 04-1010), and a power input module 88 (available from Norvell Electronics of Carrollton, Tex., part No. 04-1014). There is also a Controller PCB with logic power supply 90 (available from ENL, Inc. of Anaheim, Calif., part No. 04-1012) and an LCD module 92 (available from Microsystems Development of San Jose, Calif., part No. 04-1013). Various brackets and fasteners are utilized to secure the various components within the power supply housing. Together, the power supply module 86, the power input module 88, controller PCB 90, and LCD module 92 are collectively referred to as the power supply and controller and is configured provide power and controls to the light assembly 53.

The power supply and controller comprises push button switches for ON, OFF, START, and PAUSE functions; microcontroller for timing and function control, such as start up and cool down functions; supervisory function for power glitch and brown-out protection; memory for usage meter and storage; fan control; lamp control; speaker control for signaling elapsed time and other timed functions; power control; and I/O control and connections. In one exemplary embodiment, the power supply and controller incorporates several timed events, which can be grouped into off state, warm up state, ready state, run state, pause state, and cool down state.

For functional testing of hardware and firmware, an accelerated time mode may also be incorporated which functions like a normal state except the count down times are shortened to facilitate testing. Within the various timed states, timed events are incorporated including total usage time since last cleared; total lamp power on time; lamp warm up time before ready for use; 3–5 seconds alert or warning time before lamp is ready for use and before curing time event completes; maximum stand by time before the lamp switches into cool down mode; and count down timer for counting down the light curing period. While the various timed events can be pre-programmed for use with the bleaching composition and light assembly described herein, optionally, they can be programmed for different timed events for different bleaching composition and light source.

For longevity of the lamp 62, the fan 64 should remain on for about 2 minutes during the cool down mode subsequent to terminating power to the lamp. In one exemplary embodiment, the lamp 62 and the fan 64 are not sequenced to turn on and/or off simultaneously but rather have a short delay between the two. Among other things, this programming is performed to minimize power glitches.

When a speaker is incorporated, the speaker can be programmed to provide a low-pitch (approximately 200 Hz), a high-pitch (approximately 2 KHz), and a medium-pitch (approximately 1 KHz) to indicate different functions. For example, a high-pitch can sound off any time a button on the keypad 82 is pressed, a low-pitch can sound off when an un-programmed button or not permitted button is pressed, and a medium-pitch can sound off when an event is completed or near completion.

The power source will accommodate a 150 watt lamp. In one exemplary embodiment, the high voltage (15,000 volts) igniter has been moved from the power supply 74 to the lamp head assembly 54, thus obviating the need for wires to carry the 15,000 volts from the power supply to the lamp head assembly.

FIG. 11 is a semi-schematic perspective view of the light assembly 53, which comprises a head assembly 54 mounted on a light stand 94. In one exemplary embodiment, the light stand 94 comprises a base pole 96 and an overhang pole 98 pivotally connected together by an adjustable hinge 100. The power unit 74 is mounted to the base pole 96 and the light head 54 is mounted to the overhang pole 98. The power unit 74 and the light head 54 may be electrically communicated to one another via a cable 95 partially wired inside the two poles.

The adjustable hinge 100 allows the two poles to change the angle defined by the two pole. Optionally, the base pole 96 may include adjustable means for varying the height of the pole. The adjustable means may include telescoping devices.

A ball receiving bracket 102 mounted on an end of the overhang pole 98 is incorporated to engage the ball located on the ball mounting plate 67 of the lamp head assembly 54. In one exemplary embodiment, the ball receiving bracket 102 comprises two plates mechanically coupled to one another by an adjustable knob 104. The adjustable knob 104 allows the grip on the ball to be loosen and/or tightened to thereby permit adjustment of the position of the light head relative to the overhang pole 98.

A support base 103 comprising three or more support legs 105 may be incorporated with the base pole 96 for supporting the light stand 94. The base pole 96 may be removeably attached to the support base 103 in a socket arrangement comprising detents or a spring bias engagement means. Although the support legs 104 are shown with rollers or casters 106, short support stubs may be used for non-moveable applications.

Although the preferred embodiments of the invention have been described with some specificity, the description and drawings set forth herein are not intended to be delimiting and persons of ordinary skill in the art will understand that various modifications may be made to the embodiments discussed herein without departing from the scope of the invention, and all such changes and modifications are intended to be encompassed within the appended claims. Various changes to the lamp assembly, the power supply, and/or the tooth bleaching composition may be made including manufacturing the dimensions differently, using different materials, making the engagement or fit between the light guides and the light assembly differently, providing light guides that attach extraorally of the patient, and modifying the manner in which the base of the light guides fit inside the mouth. Accordingly, many alterations and modifications may be made by those having ordinary skill in the art without deviating from the spirit and scope of the invention.

What is claimed is:

1. A method for whitening a patient's teeth comprising the steps:
    (a) applying a dental whitening composition to the teeth;
    (b) illuminating the teeth with light from a lamp assembly; and
    (c) wherein the lamp assembly is maintained in a constant spacing relative to the teeth by a lamp guide, the lamp guide comprising a pair of spacer rods for insertion into the patient's mouth; each spacer rod comprising a first end having a foam pad configured to be positioned on one side of the patient's mouth and a second end coupled to the lamp assembly.

2. The method of claim 1, further comprising retracting the patient's lips with a lip retractor.

3. The method of claim 2, wherein the lip retractor comprises two cheek plates each comprising an arcuate race.

4. The method of claim 3, wherein the lip retractor further comprises a cross-bar.

5. The method of claim 2, further comprising adding a retractor cover over the lip retractor.

6. The method of claim 2, wherein the tip retractor comprises four cheek plates.

7. The method of claim 1, wherein the dental whitening composition comprises a two part composition.

8. The method of claim 1, wherein the lamp assembly comprises a lamp head and a power assembly mounted on a light stand comprising an adjustable hinge.

9. The method of claim 8, wherein the lamp assembly is a short arc metal halide lamp.

10. The method of claim 8, wherein the lamp head comprises an IR filter and a UV filter.

11. The method of claim 9, wherein the lamp head further comprises a diffuser filter.

12. A system for tooth bleaching comprising:
  (a) a bleaching composition comprising an oxidizing agent;
  (b) a lamp assembly comprising a light source, a light output aperture and an engagement surface;
  (c) a gap regulating device; and
  (d) wherein the bleaching composition is configured to be applied on a tooth surface of a patient and the gap regulating device is configured to couple to the patient and to the engagement surface of the lamp assembly to set a distance between the light output aperture and the tooth surface to be bleached; wherein the gap regulating device comprises a pair of rods each comprising a foam pad mounted in a first end of the rod and a second free end in abutting contact with the engagement surface of the lamp assembly.

13. The system of claim 12, wherein the bleaching composition comprises a bleaching gel and an activator gel.

14. The system of claim 13, wherein the bleaching gel and the activator gel are separately stored in a dual-barrel syringe.

15. The system of claim 12, wherein the oxidizing agent is hydrogen peroxide.

16. The system of claim 12, wherein the light source is a lamp comprising mercury gas.

17. The system of claim 12, wherein the second free end of the rod is inserted into a boss on the lamp assembly.

18. The system of claim 12, further comprising a lip retractor for retracting a patient's lips prior to application of the bleaching composition.

19. The system of claim 18, wherein the lip retractor comprises two or more cheek plates with each cheek plate comprising an arcuate race.

20. The system of claim 12, wherein the engagement surface on the lamp assembly comprises a bore.

21. The system of claim 12, wherein the gap regulating device comprises a pair of generally cylindrical rods.

22. A system for tooth bleaching comprising:
  (a) a tooth bleaching composition comprising an oxidizing agent;
  (b) a lamp assembly comprising a lamp head and a power supply box mounted on a lamp post comprising an adjustable hinge;
  (c) a spacer for setting a space between the lamp head and a patient's teeth; and
  (d) wherein the tooth bleaching composition is configured to be applied to a tooth surface to be bleached, the lamp assembly is configured to activate the oxidizing agent from the tooth bleaching composition; and the spacer is configured to set a gap between the lamp head and the patient's teeth by providing a pair of rods each comprising foam pad for a patient to bite on, a desired length for setting the gap, and a coupling end for abutting with the lamp head.

23. The system of claim 22, wherein the tooth bleaching composition comprises a two part composition separately stored in a double-barrel syringe.

24. The system of claim 23, wherein the two part composition comprises a bleaching gel comprising hydrogen peroxide and an activator gel comprising water.

25. The system of claim 22, further comprising cotton rolls or gauzes for isolating the tooth surface to be bleached.

26. The system of claim 25, further comprising a lip retractor.

27. The system of claim 26, wherein the lip retractor comprises two or more cheek plates with each cheek plate comprising an arcuate race.

28. The system of claim 27, wherein the lip retractor comprises a tongue guard.

29. The system of claim 22, wherein the lamp assembly is a short arc metal halide lamp.

30. The system of claim 29, wherein the lamp head comprises a UV filter and an IR filter.

31. The system of claim 30, wherein the lamp head further comprises a diffuser filter.

32. The system of claim 22, wherein the spacer is coupled to the lamp head by engaging a boss located on the lamp head.

33. The system of claim 22, wherein the spacer is coupled to the patient when the patient bites down on a foam pad located on an end of the spacer.

34. A system for tooth bleaching comprising:
  (a) a tooth bleaching composition comprising an oxidizing agent;
  (b) a lamp assembly comprising a lamp head and a power supply box mounted on a lamp post comprising an adjustable hinge;
  (c) a spacer for setting a space between the lamp head and a patient's teeth; and
  (d) wherein the tooth bleaching composition is configured to be applied to a tooth surface to be bleached, the lamp assembly is configured to activate the oxidizing agent from the tooth bleaching composition; and the spacer is configured to set a gap between the lamp head and the patient's teeth by securing a first end of a pair of rods between the patient's teeth and abutting a second end of the pair of rods to an engagement surface on the lamp head; and
  (e) wherein the light is activated for a 20 minute cycle and wherein the cycle is repeated two additional times with new bleaching composition applied each time.

* * * * *